US00PP24499P3

(12) United States Plant Patent
Korlipara

(10) Patent No.: US PP24,499 P3
(45) Date of Patent: May 27, 2014

(54) *LEUCANTHEMUM* PLANT NAMED 'GOLDFINCH'

(50) Latin Name: *Leucanthemum×superbum*
Varietal Denomination: Goldfinch

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 65 days.

(21) Appl. No.: 13/573,331

(22) Filed: Sep. 11, 2012

(65) Prior Publication Data

US 2014/0075623 P1 Mar. 13, 2014

(51) Int. Cl.
*A01H 5/00* (2006.01)

(52) U.S. Cl.
USPC ..... Plt./285

(58) Field of Classification Search
USPC ..... Plt./285, 284, 263.1
See application file for complete search history.

*Primary Examiner* — Kent L Bell
(74) *Attorney, Agent, or Firm* — Klarquist Sparkman, LLP

(57) ABSTRACT

A new and distinct *Leucanthemum* plant named 'Goldfinch' characterized by showy, double daisy type inflorescences, yellow ray florets that stay yellow longer than others currently on the market, excellent bloom size, a low, compact habit, and excellent vigor.

1 Drawing Sheet

Botanical denomination: *Leucanthemum×superbum.*
Variety designation: 'Goldfinch'.

BACKGROUND OF THE INVENTION

The present invention relates to a new and distinct cultivar of *Leucanthemum* and given the cultivar name 'Goldfinch'. *Leucanthemum* is in the family Asteraceae. This new cultivar originated from a controlled cross between unnamed, proprietary *Leucanthemum×superbum* seedlings. This was part of a controlled breeding program to get a long lasting yellow flowering *Leucanthemum.*

Compared to the seed parent, an unnamed proprietary seedling, the new cultivar is much shorter.

Compared to the pollen parent, an unnamed proprietary seedling, the new cultivar has yellow rather than white ray florets.

Compared to *Leucanthemum×superbum* Gold Rush™ 'Leukal' U.S. Plant Pat. No. 15,204, the new cultivar has broader ray florets, a shorter habit, and the inflorescence is yellower.

Compared to *Leucanthemum×superbum* 'Banana Cream' PPAF CPBR4203, the new cultivar has more ray florets that are yellower and stay yellow longer.

This new *Leucanthemum* cultivar is distinguished as unique with its:

1. showy, double daisy type inflorescences,
2. yellow ray florets that stay yellow longer than others currently on the market,
3. excellent bloom size,
4. a low, compact habit, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old plant growing in full sun in the garden in early July in Canby, Oreg.

DETAILED PLANT DESCRIPTION

The following is a detailed description of the new *Leucanthemum* cultivar based on observations of two-year-old specimens growing in the garden in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on *The Royal Horticultural Society Colour Chart,* $5^{th}$ edition.

Plant:

*Type.*—Herbaceous perennial.
*Hardiness.*—USDA Zones 5 to 9.
*Size.*—38 cm wide and 40 cm tall to top of inflorescences.
*Form.*—Basal clump.
*Number of crowns.*—12.
*Vigor.*—Excellent.

Stem (flowering):

*Type.*—Ascending, 1 to 6 branches per stem.
*Size.*—Grows to about 39 cm tall to a terminal inflorescence and 8 mm wide at base.
*Internode length.*—About 2 cm.
*Surface texture.*—Pubescent.
*Color.*—Yellow Green 147B.

Leaf:

*Type.*—Simple.

*Shape.*—Lanceolate.

*Arrangement.*—Alternate.

*Blade size.*—Grows to 12.3 cm long and 20 mm wide.

*Margins.*—Coarsely serrate.

*Petiole.*—Sessile.

*Apex.*—Acute.

*Base.*—Clasping.

*Surface texture.*—Pubescent on both sides.

*Venation.*—Pinnate, main vein top side Yellow Green 147B, bottom side Yellow Green 147C.

*Color.*—Topside Yellow Green 147A, bottom side Yellow Green 147B.

Inflorescence:

*Type.*—Composite on terminal stalked heads.

*Number of inflorescences per plant.*—About 25 in first flush.

*Size.*—Grows to 9 cm wide and 1.5 cm deep.

*Form.*—Ray florets are held horizontally, mature disc is rounded.

*Immature inflorescence* (*bud*).—2 cm wide and 2.1 cm deep, ovoid, ray florets held vertically and cupped inwards, Yellow 4B.

*Ray florets.*—With 1 pistil and no stamen, about 70 in number (about 11 smaller size near the disc florets), oblong, tip retuse to 4 lobed, margins entire, base obtuse, average size 37 mm long and 7 mm wide, glabrous on both sides; top and bottom side Yellow 4C blending to Yellow 4A on the apex, maturing to White 155C with tip Yellow 4A, pistil 6 mm long, ovary 1 mm long, Yellow Green 145A, style 3 mm long, Green Yellow 1C, 2 branched stigma 0.5 mm long, Yellow 2D.

*Disc.*—Slightly concave becoming convex, becoming 12 mm deep and 30 mm wide with maturity, Yellow Orange 15B.

*Disc florets.*—About 650 in number, each 7 mm long and 1.5 mm wide; corolla tubular, 6 mm long and 1.5 mm wide, 5 lobed, tips acute, margins entire, glabrous inside and out, Yellow Orange 15A on top half and Yellow Green 145A on the bottom half inside and out; pistil 1, 8 mm long, ovary 1.5 mm long and Yellow Green 145C, style 7 mm long, Yellow Orange 15A, 2 branched stigma 0.5 mm long, Yellow Orange 15A; stamen 5 in number, 4 mm long, filaments 2 mm long, Yellow Green 150D, anthers 2 mm long, Yellow Orange 17A, pollen Yellow Orange 21A.

*Phyllaries.*—About 60 in number, in 3 imbricate whorls, area 3.3 cm wide and 8 mm deep, lobes lanceolate in shape, grow to 7.5 mm long and 3 mm wide, Green 137B with margin membranous, entire, and Greyed Purple 187A, tip acute, bases adnate, glabrous on both sides.

*Receptacle.*—Grows to 20 mm wide and 4 mm deep, Yellow Green 145C.

*Bloom period.*—July through August in Canby, Oreg.

*Fragrance.*—Very slight.

*Lastingness.*—Each inflorescence lasts about two weeks in Canby, Oreg.

*Peduncle.*—Grows to 10 cm long and 5 mm wide, pubescent, Yellow Green 147A.

Seeds: None seen.

*Fertility.*—Low.

Disease and pests: The new cultivar is typical to the genus. No known resistances to pests or diseases. No problems have been found in Canby, Oreg.

I claim:

1. A new and distinct *Leucanthemum* plant as herein illustrated and described.

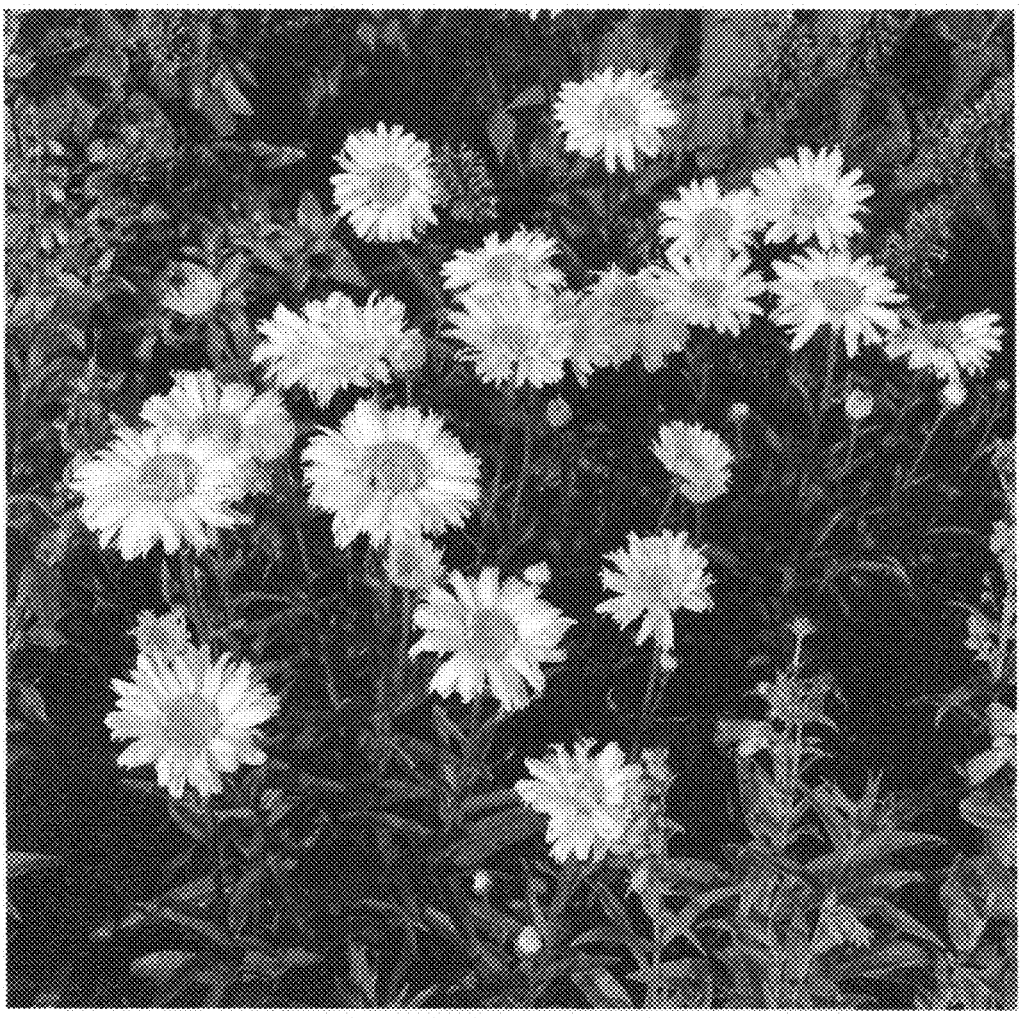

* * * * *